United States Patent [19]

Lantzsch et al.

[11] Patent Number: 4,921,529

[45] Date of Patent: May 1, 1990

[54] 2-HYDROXYETHYL-AZOLE DERIVATIVES

[75] Inventors: Reinhard Lantzsch, Wuppertal; Brandes Wilhelm, Leichlingen; Gerd Hänsller; Paul Reinecke, both of Leverkusen; Klaus Lürssen, Bergisch-Gladbach, all of Fed. Rep. of Germany

[73] Assignee: Bayer Aktiengesellschaft, Leverkusen, Fed. Rep. of Germany

[21] Appl. No.: 18,658

[22] Filed: Feb. 25, 1987

[30] Foreign Application Priority Data

Mar. 6, 1986 [DE] Fed. Rep. of Germany ....... 3607286
Jan. 28, 1987 [DE] Fed. Rep. of Germany ....... 3702301

[51] Int. Cl.$^5$ .................. A01N 43/653; C07D 249/08
[52] U.S. Cl. ........................................... 71/92; 71/76; 548/101; 548/268.6; 514/383; 514/184
[58] Field of Search ................ 548/101, 262; 514/383, 514/184; 71/92, 76

[56] References Cited

U.S. PATENT DOCUMENTS

| 4,380,546 | 4/1983 | Sauter et al. | 548/262 |
| 4,382,944 | 5/1983 | Kramer et al. | 548/262 |
| 4,507,140 | 3/1985 | Sugavanam | 548/262 |
| 4,723,984 | 2/1988 | Holmwood et al. | 548/262 |
| 4,734,126 | 3/1988 | Holmwood et al. | 548/262 |

FOREIGN PATENT DOCUMENTS

| 0040345 | 11/1981 | European Pat. Off. . |
| 0040350 | 11/1981 | European Pat. Off. . |
| 0052424 | 5/1982 | European Pat. Off. . |
| 0084834 | 8/1983 | European Pat. Off. . |
| 0150036 | 7/1985 | European Pat. Off. . |

Primary Examiner—Glennon H. Hollrah
Assistant Examiner—Patrica L. Morris
Attorney, Agent, or Firm—Sprung Horn Kramer & Woods

[57] ABSTRACT

New 2-hydroxyethyl-azole derivatives of the formula

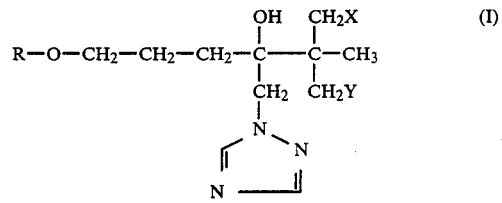

in which
R represents optionally substituted phenyl,
X represents hydrogen or halogen and
Y represents hydrogen or halogen, and acid addition salts and metal salt complexes thereof, as well as the use of the novel compounds as fungicides and plant growth regulants.

New intermediates for the synthesis of the novel 2-hydroxyethyl-azole derivatives.

11 Claims, No Drawings

2-HYDROXYETHYL-AZOLE DERIVATIVES

The present invention relates to new 2-hydroxyethyl-azole derivatives, a process for their preparation and their use as fungicides and plant growth regulators. The invention also relates to oxiranes and phenoxy-substituted ketones, processes for their preparation and their use as intermediate products for the synthesis of substances with a fungicidal and plant growth-regulating activity.

It is already known that numerous 2-hydroxyethyl-azole derivatives have fungicidal and plant growth-regulating properties (compare EP-OS (European Published Specification No.) 0,040,345). Thus, for example, 1-phenoxy-3,3-dimethyl-2-(1,2,4-triazol-1-yl-methyl)-butan-2-ol can be used for combating fungi and for regulating plant growth. When low amounts are applied, however, the action of this substance in some cases leaves something to be desired.

It is furthermore already known that phenoxypropyl ketones can be prepared by reacting phenoxypropyl-Grignard compounds with aldehydes and then oxidizing the carbinols thereby formed (compare EP-OS (European Published Specification No.) 0,150,404). The disadvantage in carrying out this process on an industrial scale is, however, that organometallic compounds are required in the context of the synthesis. It is furthermore a disadvantage that the aldehydes required as starting materials are in some cases only poorly accessible. Furthermore, oxidation of the hydroxyl group must be carried out as an additional process step. This is particularly unfavourable if the keto group in question must be reduced again to a carbinol group in the end products which are prepared from the phenoxypyropyl ketones (compare DE-OS (German Published Specification No.) 3,019,049 and DE-OS (German Published Specification No.) 3,209,431).

New 2-hydroxyethyl-azole derivatives of the formula

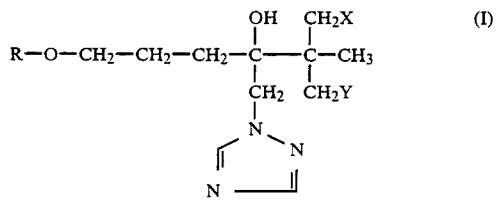

in which
R represents optionally substituted phenyl,
X represents hydrogen or halogen, and
Y represents hydrogen or halogen, and acid addition salts and metal salt complexes thereof, have now been found.

It has furthermore been found that 2-hydroxyethyl-azole derivatives of the formula (I) and acid addition salts and metal salt complexes thereof are obtained by a process in which oxiranes of the formula

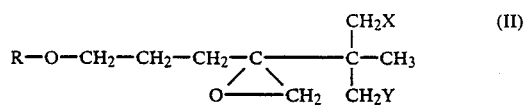

in which

R, X and Y have the abovementioned meaning, are reacted with 1,2,4-triazole of the formula

in the presence of a diluent and if appropriate in the presence of a base, and if appropriate an acid or a metal salt is subsequently added onto the compounds of the formula (I) thus obtained.

It has also been found that the new 2-hydroxyethyl-azole derivatives of the formula (I) and acid addition salts and metal salt complexes thereof have very good fungicidal and plant growth-regulating properties.

Surprisingly, the active compounds according to the invention have a clearly better fungicidal and plant growth-regulating activity than the substances known from the prior art which are structurally the most similar.

The active compounds according to the invention contain an asymmetrically substituted carbon atom and can therefore be obtained in the two optical isomer forms. The invention relates both to the isomer mixtures and to the individual isomers.

Formula (I) provides a definition of the 2-hydroxyethyl-azole derivatives according to the invention. In this formula, R preferably represents phenyl which is optionally monosubstituted, disubstituted or trisubstituted by identical or different substituents, preferred possible substituents being: halogen, alkyl with 1 to 4 carbon atoms, alkoxy with 1 to 4 carbon atoms, alkylthio with 1 to 4 carbon atoms, halogenoalkyl with 1 to 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms, cycloalkyl with 3 to 7 carbon atoms, phenyl, phenoxy and alkoximinoalkyl with 1 to 4 carbon atoms in the alkoxy group and 1 to 4 carbon atoms in the alkyl group. The substituents X and Y independently of one another preferably represent hydrogen, fluorine, chlorine or bromine.

Particularly preferred substances of the formula (I) are those in which R represents phenyl which is optionally monosubstituted, disubstituted or trisubstituted by identical or different substituents, substituents which may be mentioned being: fluorine, chlorine, bromine, methyl, ehtyl, n-propyl, n-butyl, tert.-butyl, methoxy, ethoxy, methylthio, ethylthio, trifluoromethyl, trifluoromethoxy, trifluoromethylthio, cyclopentyl, cyclohexyl, phenyl, phenoxy, methoximinomethyl and methoximinoethyl. The substituents X and Y independently of one another represent, in particular, hydrogen, fluorine or chlorine.

Addition products of acids and those 2-hydroxyethyl-azole derivatives of the formula (I) in which R, X and Y have the meanings which have already been mentioned as preferred for these substituents are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

Addition products of salts of metals of main groups II to IV and sub-groups I and II and IV to VIII of the periodic table of the elements and those 2-hydroxyethyl-azole derivatives of the formula (I) in which R, X and Y have the meanings which have already been mentioned as preferred for these substituents are also preferred compounds according to the invention.

Salts of copper, zinc, manganese, magnesium, tin, iron and nickel are particularly preferred here. Possible anions of these salts are those which are derived from those acids which lead to physiologically acceptable addition products. Particularly preferred acids of this type are, in this connection, the hydrogen halide acids, such as, for example, hydrochloric acid and hydrobromic acid, and furthermore phosphoric acid, nitric acid and sulphuric acid.

If 2-(1,1-dimethyl-ethyl)-2-(3-phenoxy-propyl)oxirane and 1,2,4-triazole are used as starting substances, the course of the process according to the invention can be represented by the following equation:

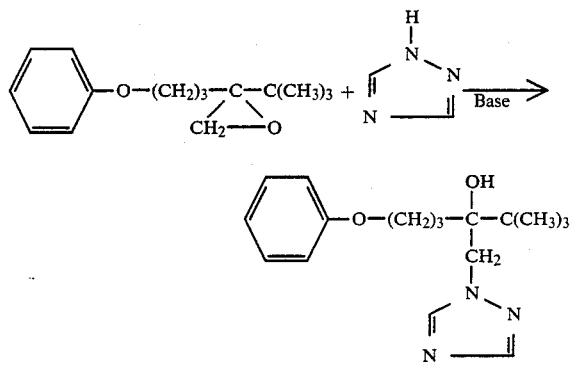

Formula (II) provides a general definition of the oxiranes required as starting substances in carrying out the process according to the invention. In this formula, R, X and Y preferably have those meanings which have already been mentioned as preferred for these substituents in the description of the substances of the formula (I) according to the invention.

The oxiranes of the formula (II) are new. They can be prepared by a process in which phenoxypropyl ketones of the formula

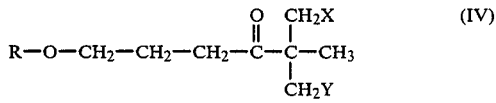

in which
R, X and Y have the abovementioned meaning, are reacted with trimethylsulphonium iodide or trimethylsulphonium methosulphate in the presence of a base, such as, for example, potassium tert.-butylate, potassium hydroxide or sodium hydride, and in the presence of a diluent, such as, for example, dimethylsulphoxide, acetonitrile or tetrahydrofuran, at temperatures between 0° C. and 60° C.

Formula (IV) provides a definition of the phenoxypropyl ketones required as starting substances in the above process. In this formula, R, X and Y preferably have those meanings which have already been mentioned as preferred for these substituents in connection with the description of the substances of the formula (I) according to the invention.

The phenoxypropyl ketones of the formula (IV) are known in some cases (compare EP-OS (European Published Specification No.) 0,150,404). They can be prepared by a new process, by a procedure in which acid halides of the formula

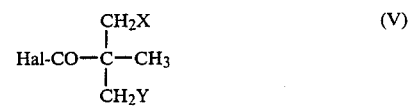

in which
X and Y have the abovementioned meaning and
Hal represents halogen,
are reacted with phenoxypropargyl compounds of the formula

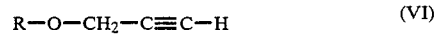

in which
R has the abovementioned meaning,
if appropriate in the presence of a diluent and if appropriate in the presence of an acid-binding agent and if appropriate in the presence of a catalyst, and the phenoxy-substituted ketones thereby formed, of the formula

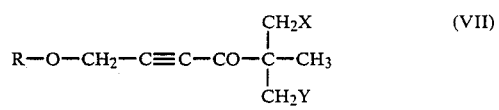

in which
R, X and Y have the abovementioned meaning,
are reacted with hydrogen in the presence of a hydrogenation catalyst and in the presence of a diluent.

Surprisingly, the phenoxypropyl ketones of the formula (IV) can be prepared in higher yields by the above process than by the processes previously known. Moreover, the new process is distinguished from the corresponding methods already described by a number of advantages. Thus, the starting materials required are easy to handle and also accessible in relatively large amounts. It is also an advantage that working with organometallic compounds is avoided. Furthermore, no intermediate oxidation of carbinol groups which are reduced again, if appropriate, in the synthesis of the end products is necessary.

If pivaloyl chloride and 4-chlorophenyl propargyl ether are used as starting substances in the above process, copper (II) chloride is used as the catalyst and the 2,2-dimethyl-6-(4-chlorophenoxy)-hex-4-in-3-one thereby formed is hydrogenated with hydrogen in the presence of Raney nickel, the course of the reaction can be illustrated by the following equation:

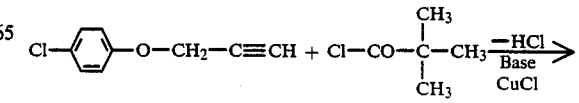

-continued

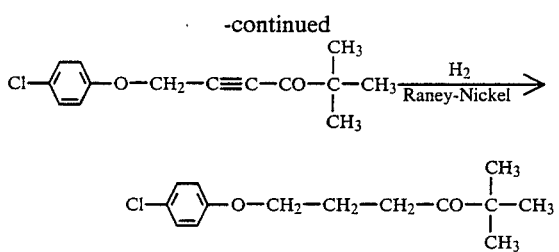

Formula (V) provides a definition of the acid halides required as starting substances in the above process. In this formula, X and Y preferably have those meanings which have already been mentioned as preferred for these substituents in connection with the description of the substances of the formula (I) according to the invention. Hal preferably represents chlorine, bromine or iodine.

The acid halides of the formula (V) are known or can be prepared by processes which are known in principle (compare U.S. Pat. No. 3,414,612, DE-OS (German Published Specification No.) 3,128,445 and EP-OS (European Published Specification No.) 0,049,416).

Formula (VI) provides a definition of the phenoxypropargyl compounds furthermore required as starting substances in the above process. In this formula, R preferably has those meanings which have already been mentioned as preferred for these substituents in connection with the description of the substances of the formula (I) according to the invention.

The phenoxypropargyl compounds of the formula (VI) are likewise known or can be prepared in a simple manner by processes which are known in principle (compare Houben-Weyl "Methoden der organischen Chemie" ("Methods of Organic Chemistry"), Volume V, 2a, page 654).

The phenoxy-substituted ketones of the formula (VII) formed as intermediate products in the above process are new.

Possible diluents in carrying out the first stage of the above process are inert organic solvents. Aromatic hydrocarbons, such as toluene, xylene or chlorobenzene, and furthermore nitriles, such as acetonitrile, and also ethers, such as diisobutyl ether and dioxane, and moreover pyridine, can preferably be used.

Preferred possible acid-binding agents in carrying out the first stage of the above process are tertiary amines. Triethylamine, N,N-dimethylcyclohexylamine and N,N-dimethylbenzylamine are particularly preferred.

The reaction temperatures can be varied within a substantial range in carrying out the first stage of the above process. The reaction is in general carried out at temperatures between 0° C. and 150° C., preferably between 20° C. and 120° C.

Preferred possible catalysts in carrying out the first stage of the above process are copper-(I) chloride and copper-(I) bromide.

In carrying out the first stage of the above process, the compounds of the formulae (V) and (VI) are employed in approximately equimolar amounts. However, it is also possible to use one or other of the components in an excess. In many cases, it is advisable to carry out the reaction in the presence of an acid-binding agent and in the presence of a substance with a catalytic action. Working up and isolation of the phenoxy-substituted ketones of the Formula (VII) are carried out by customary methods.

The second stage of the above process for the preparation of phenoxy-propyl ketones of the formula (IV) is carried out in the liquid phase, preferably in the presence of diluents, using a suspended pulverulent hydrogenation catalyst. The hydrogenation can be carried out discontinuously (batchwise) or continuously as bottom phase or trickle phase hydrogenation in known hydrogenation reactors, such as autoclaves, autoclave cascades, tube reactors or ciruclatory reactors. The preferred procedure is discontinuous bottom phase hydrogenation in an autoclave under increased pressure.

Possible diluents in carrying out the hydrogenation in the second stage of the above process are inert organic solvents. Solvents which can preferably be used are alcohols, such as methanol, ethanol, isopropanol or ethylene glycol, and furthermore ethers, such as diethyl ether, diisopropyl ether, ethylene glycol monomethyl ether, ethylene glycol dimethyl ether, dioxane or tetrahydrofuran; saturated hydrocarbons, such as n-heptane or cyclohexane; and esters, such as ethyl acetate.

Hydrogenation catalysts which are suitable for the above process are, for example, those which consist of metals and/or compounds of elements of the eighth subgroup of the Medeleev periodic table of the elements or which contain these. The metals ruthenium, rhodium, palladium, platinum, cobalt and nickel and compounds thereof are preferred here. The metal compounds can be, for example, oxides, hydroxides and/or hydrated oxides. The metals copper,vanadium, molybdenum, chromium and/or manganese and compounds of these metals can addtionally be present.

The hydrogenation catalysts can consist exclusively or predominantly of hydrogen transfer substances, but these can also be applied to support materials.

Possible support materials for the hydrogen transfer substances are, for example: inorganic materials, such as kieselguhr, silica, aluminium oxide, alkali metal and alkaline earth metal silicates, aluminium silicates, montmorillonite, zeolites, spinels, dolomite, kaolin, magnesium silicates, zirconium oxide, zinc oxide, calcium carbonate, silicon carbide, aluminium phosphate, boron phosphate, asbestos, active charcoal or barium sulphate, or organic materials, for example naturally occurring or synthetic compounds with high molecular weights, such as silk, polyamides, polystyrenes, cellulose or polyurethanes. Inorganic support materials in powder form are preferred.

Such supported catalysts can in general contain 0.5 to 50% by weight, preferably 1 to 10% by weight, of the hydrogen transfer substance, based on the total weight of the supported catalyst. The hydrogen transfer substance can thereby be distributed homogeneously in the support material, but catalysts in which the hydrogen donor substance is deposited in the outer layer or on the surface are preferred. The preparation and shaping of the catalysts which can be used in the above process can be carried out in a known manner (see, for example, Houben-Weyl, Methoden der organischen Chemie (Methods of Organic Chemistry), Volume IV, Ic, Part I, pages 16 to 26, Georg Thieme Verlag, Stuttgart 1980).

Preferred supported catalysts are ruthenium-on-charcoal, ruthenium-on-aluminium oxide, rhodium-on-charcoal, rhodium-on-aluminium oxide, palladium-on-calcium carbonate, palladium-on-barium sulphate, palladium-on-silica, platinum-on-charcoal and platinum-on-aluminium oxide, nickel-on-kieselguhr, nickel-onaluminium oxide and nickel and palladium-on-aluminium oxide.

Preferred hydrogenation catalysts which consist exclusively or predominantly of hydrogen transfer substance are, for example, oxidic catalysts, such as palladium oxide, platinum oxide, ruthenium oxide and/or rhodium oxide/platinum oxide according to Nishimura, and furthermore black catalysts which can be prepared by reduction of corresponding metal salts or metal salt mixtures with alkali metal hydrides, alkali metal boranates, metal alkyls, hydrazine, formaldehyde, hydrogen or electropositive metals, such as palladium black, platinum black and rhodium black; as well as skeleton catalysts of the Raney type, such as Raney nickel, Raney cobalt, Raney nickel/cobalt, Raney nickel/iron, Raney nickel/copper, Raney nickel/iron/chromium, Raney nickel/palladium and Raney nickel/iron/vanadium.

Catalysts which contain nickel and/or palladium or consist of these are particularly preferred.

The hydrogenation catalysts are employed for carrying out the second stage of the above process in a amount such that 0.05 to 2.5, preferably 0.1 to 1% by weight of hydrogen transfer substance is present, based on the total weight of the reaction mixture.

Mixtures of two or more of the hydrogenation catalysts mentioned can also be used for carrying out the above process.

The catalytic activity of the hydrogenation catalysts is in general largely retained when carrying out the above process, so that these can be employed repeatedly in the case of a discontinuous procedure and can remain in use for a prolonged period in the case of a continuous procedure.

The reaction temperatures can be varied within a relatively wide range in carrying out the hydrogenation in the second stage of the above process. The reaction is in general carried out at temperatures between 0° C. and 150° C., preferably between 20° C. and 60° C.

The hydrogenations in the above process are preferably carried out under increased pressure. They are in general carried out under pressures between 1 and 150 bar, preferably between 20 and 80 bar.

The reaction time required for the above hydrogenation depends on the reaction temperature, the partial pressure of hydrogen, the intensity of mixing of the reaction mixture and the activity and concentration of the hydrogenation catalyst. The reaction time required is in general in the range from 15 minutes to several hours.

In the simplest embodiment, the hydrogenation in the second stage of the above process can be carried out, for example, discontinuously in the following manner: an autoclave which is equipped with a stirring or mixing device and can be heated is charged in a suitable manner with a phenoxy-substituted ketone of the formula (VII), the hydrogenation catalyst and the diluent. When the autoclave has been deaerated and then hydrogen has been forced in up to the desired pressure, the mixture is heated at the chosen reaction temperature, with intense mixing. The course of the reaction can easily be monitored by measuring the consumption of hydrogen, which is compensated by further addition of hydrogen. The hydrogenation has ended when no further hydrogen is consumed and the amount of hydrogen consumed approximately corresponds to the amount of hydrogen theoretically required.

When the hydrogenation has ended, the reaction mixture is cooled, let down and worked up in a known manner, for example by filtering off the catalyst and distilling off the diluent.

The phenoxypropyl ketones of the formula (IV) are not only suitable as intermediate products for the preparation of the substances of the formula (I) according to the invention but can also be used for the synthesis of other substances with fungicidal and plant growth-regulating properties (compare EP-OS (European Published Specification No.) 0,150,404).

The oxiranes of the formula (II) can be further reacted directly, if appropriate without isolation, in the process according to the invention for the preparation of 2-hydroxyethyl-azole derivatives of the formula (I).

Possible diluents for the process according to the invention for the preparation of 2-hydroxyethyl-azole derivatives of the formula (I) are all the inert organic solvents. Solvents which can preferably be used are alcohols, such as ethanol and methoxyethanol; ketones, such as, for example, 2-butanone; nitriles, such as, for example, acetonitrile; esters, such as, for example, ethyl acetate; ethers, such as, for example, dioxane; aromatic hydrocarbons, such as, for example, benzene and toluene; or amides, such as, for example, dimethylformamide.

Possible bases for the reaction according to the invention are all the inorganic and organic bases which can usually be employed. These include, preferably, alkali metal carbonates, such as, for example, sodium carbonate and potassium carbonate; alkali metal hydroxides, such as, for example, sodium hydroxide; alkali metal alcoholates, such as, for example, sodium methylate and ethylate and potassium methylate and ethylate; alkali metal hydrides, such as, for example, sodium hydride; and lower tertiary alkylamines, cycloalkylamines and aralkylamines, such as, in particular, triethylamine.

The reaction temperatures can be varied within a substantial range in carrying out the process according to the invention. The reaction is in general carried out at temperatures between 0° and 200° C., preferably between 60° and 150° C.

In carrying out the process according to the invention, 1 to 2 mol of 1,2,4-triazole and, if appropriate, 1 to 2 mol of base are preferably employed per mol of oxirane of the formula (II). The end products are isolated in the generally customary manner.

The compounds of the formula (I) obtainable by the process according to the invention can be converted into acid addition salts or metal salt complexes.

Those acids which have already been mentioned as preferred acids in connection with the description of the acid addition salts according to the invention are preferably suitable for the preparation of acid addition salts of the compounds of the formula (I).

The acid addition salts of the compounds of the formula (I) can be obtained in a simple manner by customary salt formation methods, for example by dissolving a compound of the general formula (I) in a suitable inert solvent and adding the acid, for example hydrochloric acid, and they can be isolated in a known manner, for example by filtration, and if appropriate purified by washing with an inert organic solvent.

Those salts of metals which have already been described above are preferably suitable for the preparation of metal salt complexes of the compounds of the general formula (I).

The metal salt complexes of compounds of the general formula (I) can be obtained in a simple manner by customary processes, thus, for example, by dissolving the metal salt in alcohol, for example ethanol, and adding the solution to the compounds of the general formula (I). The metal salt complexes can be isolated in a known manner, for example by filtration, and if appropriate purified by recrystallization.

The active compounds according to the invention have a powerful microbicidal action and can be employed as fungicides.

Fungicidal agents are employed in plant protection for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but no by way of limitation: Xanthomanas species, such as, for example, Xanthomonas campestris pv. oryzae; Pseudomonas species, such as, for example, Pseudomonas syringae pv. Lachrymans; Erwinia species, such as, for example, Erwinia amylovora; Pythium species, such as, for example, Pythium ultimum; Phytophthora species, such as, for example, Phytophthora infestans; Pseudoperonospora species, such as, for example, Pseudoperonospora humuli or Pseudoperonospora cubense; Plasmopara species, such as, for example, Plasmopara viticola; Peronospora species, such as, for example, Peronospora pisi or P. brassicae; Erysiphe species, such as, for example, Erysiphe graminis; Sphaerotheca species, such as, for example, Sphaerotheca fuliginea; Podosphaera species, such as, for example, Podosphaera Leucotricha; Venturia species, such as, for example, Venturia inaequalis; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention also have plant growth-regulating properties.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of bending ("Lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simulteneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Usuing growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the colouration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizinzing, scattering, dusting, foaming, brushing on and the like. It is furthermore possible to apply the active compounds by the ultra-low volume method or to inject the active compound formulation or the active compound itself into the soil. The seeds of the plants can also be treated.

When the substances according to the invention are used as fungicides, the amount applied can be varied within a substantial range depending on the nature of the application. Thus, the active compound concentrations in the use forms in the treatment of parts of plants are in general between 1 and 0.0001% by weight, preferably between 0.5 and 0.001%. In the treatment of seed, amounts of active compound of 0.001 to 50 g per kilogram of seed, preferably 0.01 to 10 g, are in general required. In the treatment of soil, active compound concentrations of 0.00001 to 0.1% by weight, preferably 0.0001 to 0.02%, are required at the place of action.

When the compounds according to the invention are used as plant growth regulators, the amounts applied can be varied within a substantial range. In general, 0.01 to 50 kg, preferably 0.05 to 10 kg, of active compound are used per hectare of soil surface.

When the substances according to the invention are used as plant growth regulators, they are applied within a preferred period of time, the exact definition of which depends on the climatic and vegetative circumstances.

PREPARATION EXAMPLES

EXAMPLE 1

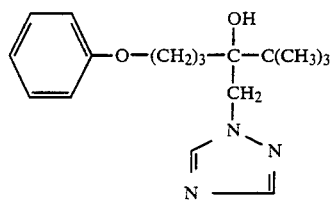
(I-1)

5.6 g (0.082 mol) of 1,2,4-triazole are added to a suspension of 11.3 g (0.082 mol) of potassium carbonate in 50 ml of dimethylformamide. 8.8 g (0.038 mol) of 2-(1,1-dimethyl-ethyl)-2-(3-phenoxypropyl)-oxirane are then added dropwise to the mixture, and the mixture is heated at 130° to 140° C. for 12 hours. After cooling to room temperature, the reaction mixture is filtered. The filtrate is concentrated under reduced pressure and the residue which remains is dissolved in methylene chloride. The organic phase is washed three times with water and, after drying, is concentrated. The residue is recrystallized from n-hexane. 8.1 g (70.3% of theory) of 2,2-dimethyl-6-phenoxy-3-(1,2,4-triazol-1-yl-methyl)-hexan-3-ol of melting point 106° C. are obtained in this manner.

Preparation of starting substances:

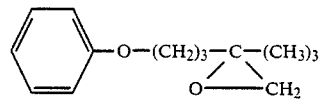
(II-1)

9 g (41 mMol) of 2,2-dimethyl-6-phenoxy-hexan-3-one are added dropwise to a mixture of 5.5 g (49 mMol) of potassium tert.-butylate in 40 ml of tetrahydrofuran at room temperature, with stirring, whereupon a clear yellowish solution forms. 12.5 g (61.5 mMol) of trimethylsulphonium iodide are then added and the mixture is stirred at 20° to 25° C. for 12 hours. Thereafter, the reaction mixture is filtered and the filtrate is concentrated under reduced pressure. The residue which remains is taken up in methylene chloride and the resulting solution is washed three times with water. After the organic phase has been dried, the solvent is stripped off. 7.8 g (81% of theory) of 2-(1,1-dimethyl-ethyl)-2-(3-phenoxypropyl)-oxirane are obtained in this manner in the form of a liquid of refractive index $nD^{20} = 1.503$.

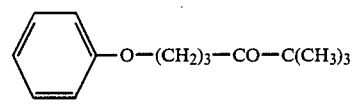
(IV-1)

20 g (0.0926 mol) of 2,2-dimethyl-6-phenoxy-hex-4-in-3-one are dissolved in 180 ml of methanol, and 5 g of Raney nickel are added. The mixture is hydrogenated with hydrogen under a pressure of 50 to 60 bar at 37° C. The hydrogenation has ended after 40 minutes. The reaction mixture is filtered and the filtrate is concentrated by stripping off the solvent under reduced pressure. 19.5 g (95.7% of theory) of 2,2-dimethyl-6-phenoxy-hexan-3-one are obtained in this manner.

$^1$H-NMR(CDCl$_3$): s(9H) at 1.1 ppm; m (2H) at 2.05 ppm, t(2H) at 2.7 ppm, t (2H) at 3.95 ppm and m(5H) at 6.85–7.3 ppm.

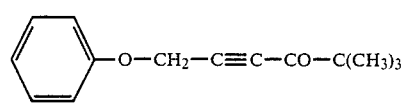
(VII-1)

13.2 g (0.1 mol) of phenyl propargyl ether are added dropwise to a mixture of 10.1 g (0.1 mol) of triethylamine and 1.43 g of copper-(I) bromide in 60 ml of toluene at 20° C., under a nitrogen atmosphere and with stirring. The mixture is subsequently stirred at 20° C. for 30 minutes. Thereafter, 12 g (0.1 mol) of pivaloyl chloride are added dropwise in the course of 15 minutes. The reaction mixture is heated to 80° C. and is stirred at this temperature for 10 hours. After cooling to room temperature, the reaction mixture is washed first with dilute aqueous hydrochloric acid and then with water. The organic phase is concentrated by stripping off the solvent and the residue which remains is distilled under a high vacuum. 16 g (75% of theory) of 2,2-dimethyl-6-phenoxyhex-4-in-3-one are obtained in this manner in the form of a liquid.

Boiling point = 125° C./0.05 mbar (bulb tube)

The compounds listed in the following examples are also obtained by the method described in Example 1.

EXAMPLE 2

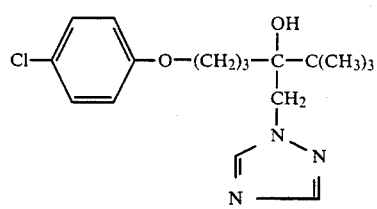
(I-2)

Melting point: 87° C.

EXAMPLE 3

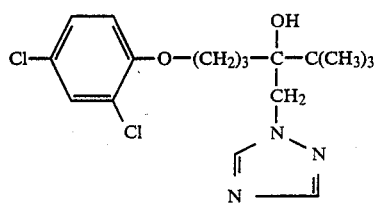 (I-3)

Oil

EXAMPLE 4

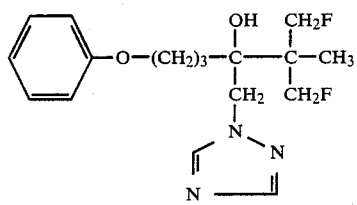

The starting materials, which are shown in the following Examples are also prepared according to the method of Example 1.

EXAMPLE 5

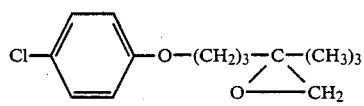 (II-2)

$n_D^{20} = 1.515$

EXAMPLE 6

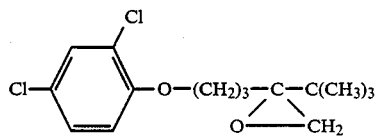 (II-3)

$n_D^{20} = 1.529$

EXAMPLE 7

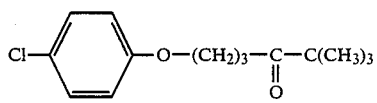 (IV-2)

$n_D^{20} = 1.509$

EXAMPLE 8

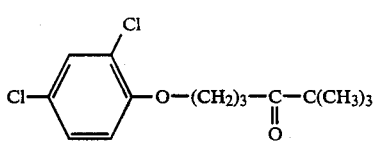 (IV-3)

$n_D^{20} = 1.512$

EXAMPLE 9

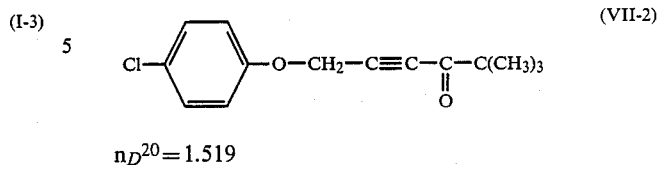 (VII-2)

$n_D^{20} = 1.519$

EXAMPLE 10

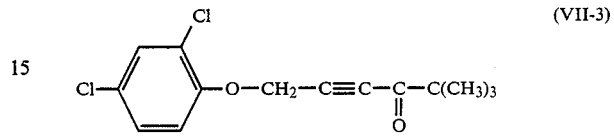 (VII-3)

$n_D^{20} = 1.535$

The substance of the formula shown below was employed as comparison compound in the following Examples:

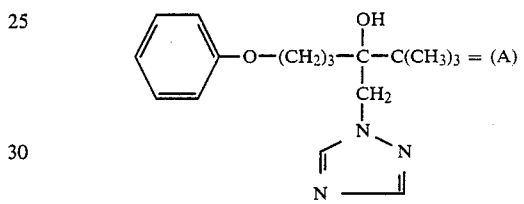

(known from EP-OS (European Published Specification) No. 0,040,345)

EXAMPLE A

Inhibition of growth of cotton

Solvent: 30 parts by weight of dimethylformamide
Emulsifier: 1 part by weight of polyxyethylene sorbitan monolaurate To produce a suitable preparation of active compound, 1 part by weight of active compound was mixed with the stated amount of solvent and emulsifier and the mixture was made up to the desired concentration with water.

Cotton plants are grown in a greenhouse until the 5th secondary leaf has unfolded completely. In this stage, the plants are sprayed with the preparation of active compound until dripping wet. After 2 weeks, the additional growth of the plants is measured and the inhibition of growth in per cent of the additional growth of the control plants is calculated. 100% inhibition of growth means that growth has stopped and 0% denotes a growth corresponding to that of the control plants.

In this test, the active compound according to the invention of the formula (I-1) shows a significantly better activity than the comparison compound (A).

EXAMPLE B

Growth of sugar beet

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Sugar beet plants are grown in a greenhouse until formation of the cotyledon is complete. In this stage, the plants are sprayed with the preparations of active compound until dripping wet. After 14 days, the additional growth of the plants is measured and the growth in per cent of the additional growth of the control plants is calculated. 100% of growth denotes a growth which corresponds to that of the control plants, values over a 100% denote an increase of the growth compared with the control plants and 0% denotes that growth has stopped.

In this test, the active compound according to the invention of the formula (I-1) shows a better activity than the comparison compound (A).

EXAMPLE C

Pyricularia Test (rice)/protective

Solvent: 12.5 parts by weight of acetone
Emulsifier: 0.3 parts by weight of alkylarylpolyglycolether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried off, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, the active compound according to the invention of the formula (I-1) shows a significantly better activity than the comparison compound (A).

EXAMPLE D

Puccinia Test (wheat)/protective

Solvent: 100 parts by weight of dimethylformamide
Emulsifier: 0.25 parts by weight of alkylarylpolyglycolether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita in a 0.1% strength aqueous agar solution. After the spore suspension has dried on, the plants are sprayed with the preparation of active compound until dew-moist. The plants remain in an incubation cabin at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, the active compound according to the invention of the formula (I-1) shows a significantly better activity than the comparison compound (A).

EXAMPLE E

Venturia test (apple) / protective

Solvent: 4.7 parts by weight of acetone
Emulsifier: 0.3 parts by weight of alkylarylpolyglycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the active compound according to the invention of the formula (I-1) shows a significantly better activity than the comparison compound (A).

It will be understood that the specification and examples are illustrative but not limitative of the present invention and that other embodiments within the spirit and scope of the invention will suggest themselves to those skilled in the art.

What is claimed is:

1. A 2-Hydroxyethyl-azole derivative of the formula $$R-O-CH_2-CH_2-CH_2-\underset{\underset{N\diagup\diagdown N}{\overset{|}{\underset{\|}{N}}}}{\overset{OH}{\underset{CH_2}{\overset{|}{C}}}}-\overset{CH_2X}{\underset{CH_2Y}{\overset{|}{C}}}-CH_3$$

in which
R is phenyl or mono- or di-substituted phenyl, the substituents being selected from the group consisting of halogen, alkyl with 1 to 4 carbon atoms, alkylthio with 1 to 4 carbon atoms, and cycloalkyl with 3 to 7 carbon atoms,
X represents hydrogen and
Y represents hydrogen, and an acid addition salt or a metal salt complex thereof.

2. A 2-hydroxyethyl-azole derivative as claimed in claim 1, wherein
R is phenyl, or mono-, or di-substituted phenyl, the substituents being selected from the group consisting of fluorine, chlorine, bromine, methyl, ethyl, n-propyl, n-butyl, tert.-butyl, methylthio, ethylthio, cyclopentyl, and cyclohexyl,
X is hydrogen, and
Y is hydrogen.

3. A 2-hydroxyethyl-azole derivative as claimed in claim 1, wherein such compound is 2,2-dimethyl-6-phenoxy-3-(1,2,4-triazol-1-yl-methyl)-hexan-3-ol of the formula

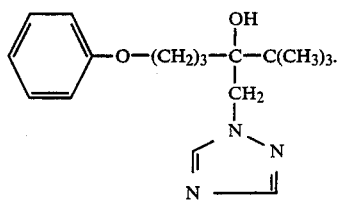

4. A 2-hydroxyethyl-azole derivative as claimed in claim 1, wherein such compound is 2,2-dimethyl-6-(4-chlorophenoxy)-3-(1,2,4-triazol-1-yl-methyl)-hexan-3-ol of the formula

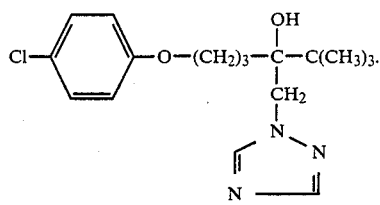

5. A 2-hydroxyethyl-azole derivative as claimed in claim 1, wherein such compound is 2,2-dimethyl-6-(2,4-dichlorophenoxy)-3-(1,2,4-triazol-1-yl-methyl)-hexan-3-ol of the formula

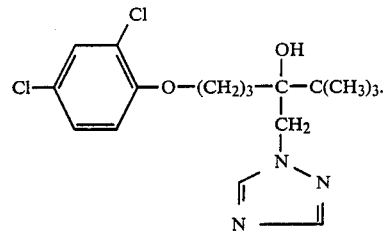

6. A fungicidal composition comprising a fungicidally effective amount of a compound according to claim 1 in admixture with an inert diluent.

7. A method of combating fungi comprising applying to the fungi, or to a habitat thereof, a fungicidally effective amount of a compound according to claim 1.

8. The method according to claim 7, wherein such compound is
2,2-dimethyl-6-phenoxy-3-(1,2,4-triazol-1-yl-methyl)-hexan-3-ol,
2,2-dimethyl-6-(4-chloro-phenoxy)-3-(1,2,4-triazol-1-yl-methyl)-hexan-3-ol or
2,2-dimethyl-6-(2,4-dichloro-phenoxy)-3-(1,2,4-triazol-1-yl-methyl)-hexan-3-ol.

9. A plant growth regulating composition comprising a plant growth regulating effective amount of a compound according to claim 1 in admixture with an inert diluent.

10. A method of regulating the growth of plants comprising applying to the plants or to their habitat a plant growth regulating effective amount of a compound according to claim 1.

11. The method according to claim 10, wherein such compound is
2,2-dimethyl-6-phenoxy-3-(1,2,4-triazol-1-yl-methyl)-hexan-3-ol,
2,2-dimethyl-6-(4-chloro-phenoxy)-3-(1,2,4-triazol-1-yl-methyl)-hexan-3-ol or
2,2-dimethyl-6-(2,4-dichloro-phenoxy)-3-(1,2,4-triazol-1-yl-methyl)-hexan-3-ol.

* * * * *

UNITED STATES PATENT AND TRADEMARK OFFICE
CERTIFICATE OF CORRECTION

PATENT NO. : 4,921,529

DATED : May 1, 1990

INVENTOR(S) : Reinhard Lantzsch, et al.

It is certified that error appears in the above-identified patent and that said Letters Patent is hereby corrected as shown below:

ON THE TITLE PAGE

Item [75] Inventors: line 2, delete "Brandes Wilhelm" and substitute --Wilhelm Brandes--;

line 3, delete "Hänsller" and substitute --Hänssler--

Signed and Sealed this

Third Day of March, 1992

Attest:

HARRY F. MANBECK, JR.

Attesting Officer

Commissioner of Patents and Trademarks